US00PP32279P3

(12) United States Plant Patent

Eveleens et al.

(10) Patent No.: US PP32,279 P3
(45) Date of Patent: Oct. 6, 2020

(54) *HYDRANGEA* PLANT NAMED 'HOKOMAREDA'

(50) Latin Name: *Hydrangea macrophylla*
Varietal Denomination: Hokomareda

(71) Applicants: Horteve Breeding BV, Aalsmeer (NL); Kolster Holding BV, Boskoop (NL)

(72) Inventors: Cornelis Pieter Eveleens, Aalsmeer (NL); Peter Rudolf Kolster, Boskoop (NL)

(73) Assignees: HORTEVE BREEDING BV, Aalsmeer (NL), part interest; KOLSTER HOLDING BV, Boskoop (NL), part interest ( * ) Notice: Subject to any disclaimer, the term of this patent is extended or adjusted under 35 U.S.C. 154(b) by 0 days.

(21) Appl. No.: 16/501,725

(22) Filed: May 29, 2019

(65) Prior Publication Data

US 2020/0170160 P1 May 28, 2020

(30) Foreign Application Priority Data

Nov. 27, 2018 (QZ) ..... PBR 2018/3094

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ... A01H 5/02; A01H 5/00; A01H 6/48; A01H 1/02
See application file for complete search history.

(56) References Cited

PUBLICATIONS

EuroFlora 2018 *Hydrangea* Magical "Red Amethyst" Hokomareda *Hydrangea* Magical Red Amethyst New !!!!, retrieved Feb. 5, 2020, retrieved from Internet http://euroflora.in.ua/product/gortenziya-makrofila-hydrangea-magical-red-amethyst-novinka/, 2 pp. including English translation (Year: 2018).*
Upov Pluto Plant Variety Database Jan. 29, 2020, retrieved on Feb. 5, 2020, retrieved from the Internet at https://www.upov.int/pluto/en/index.jsp, one page. (Year: 2020).*

* cited by examiner

*Primary Examiner* — June Hwu
(74) *Attorney, Agent, or Firm* — Penny J. Aguirre

(57) ABSTRACT

A new cultivar of *Hydrangea macrophylla* plant named 'Hokomareda' that is characterized by its flattened mophead type inflorescences with sterile flower sepals that are deep pink to red in color with hints of green, its sturdy and thick textured sterile flower sepals, its good performance as a cut flower and a container plant, and its upright plant habit.

2 Drawing Sheets

Botanical classification: *Hydrangea macrophylla.*
Varietal denomination: 'Hokomareda'.

CROSS REFERENCE TO A RELATED APPLICATIONS

This application claims priority to European Community Plant Variety Office (CPVO) Plant Breeder's Rights Application No. 2018/3094 filed on Nov. 27, 2018, the entire contents of which is incorporated by reference herein. This application is also related to U.S. Plant Patents for plants derived from the same breeding program that are entitled *Hydrangea* Plant Named 'Hokomathyst' (U.S. Plant Pat. No. 22,261), *Hydrangea* Plant Named 'Hokomac' (U.S. Plant Pat. No. 22,259), and *Hydrangea* Plant Named 'Hortmagreclo' (U.S. Plant Pat. No. 28,063).

BACKGROUND OF THE INVENTION

The present invention relates to a new and distinct cultivar of *Hydrangea macrophylla* and will be referred to hereafter by its cultivar name, 'Hokomareda'. 'Hokomareda' represents a new mophead type *Hydrangea*, a deciduous shrub grown for use as a landscape plant.

'Hokomareda' was derived from an ongoing controlled breeding program directed by the Inventors in Boskoop, The Netherlands. The Inventors discovered the new cultivar in June of 2013 as a naturally occurring branch mutation of *Hydrangea macrophylla* 'Hokomathyst' that was growing outdoors in a container in Boskoop, The Netherlands.

Asexual propagation of the new cultivar was first accomplished by stem cuttings by one of the Inventors in June of 2013 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomareda' as a unique cultivar of *Hydrangea macrophylla.*

1. 'Hokomareda' exhibits flattened mophead type inflorescences with sterile flower sepals that are deep pink to red in color with hints of green.
2. 'Hokomareda' exhibits sturdy and thick textured sterile flower sepals.

3. 'Hokomareda' performs well as a cut flower and a container plant.
4. 'Hokomareda' exhibits an upright plant habit.

The parent plant of 'Hokomareda', 'Hokomathyst', differs from 'Hokomareda' in having sterile flower sepals that are pinker in color with green margins. 'Hokomareda' can be most closely compared to the *Hydrangea macrophylla* cultivars 'Hokomac' and 'Hortmagreclo'. Both are similar to 'Hokomareda' in having flattened inflorescences, an upright plant habit, and sterile sepals that are sturdy. 'Hokomac' differs from 'Hokomareda' in having sterile flower sepals that are lighter in color and more pink. 'Hortmagreclo' differs from 'Hokomareda' in having sterile sepals that are green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of the new *Hydrangea*. The photographs were taken of a plant two years in age as grown in a 17-cm container in a greenhouse in Boskoop, The Netherlands.

The photograph in FIG. 1 provides a side view of the plant habit of 'Hokomareda' in bloom.

Figure 1:
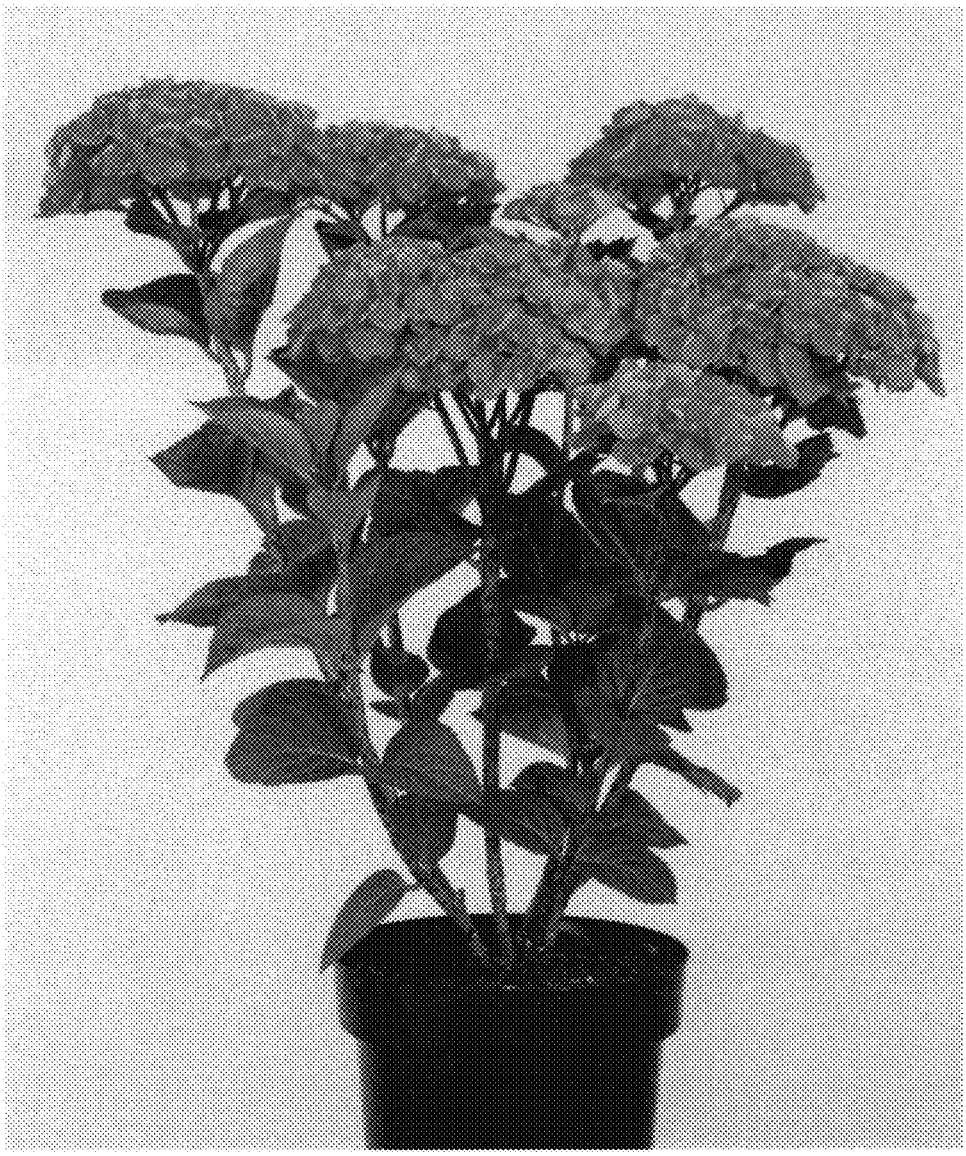
Figure 2:
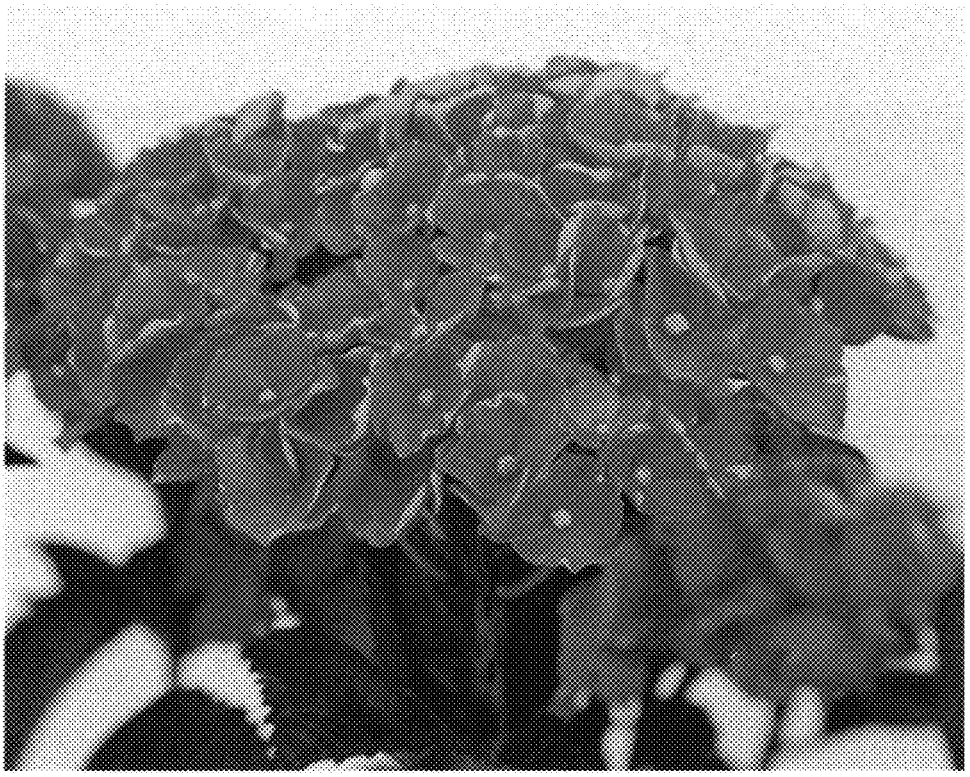

The photograph in FIG. 2 provides a close-up view of an inflorescence of 'Hokomareda'.

Figure 3:
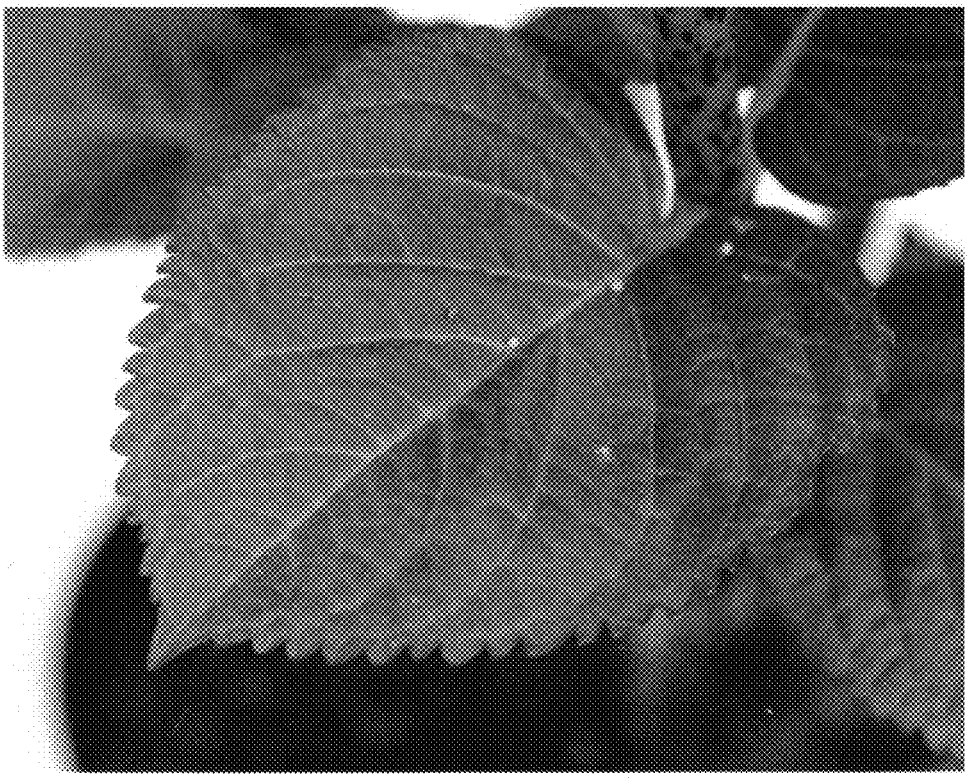

The photograph in FIG. 3 provides a close-up view of a leaf of 'Hokomareda'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants two years in age as grown in 17-cm containers in a greenhouse in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—2 months from late summer into fall in The Netherlands.

*Plant type.*—Perennial shrub, mophead type *Hydrangea.*

*Plant habit.*—Upright spreading, sturdy.

*Height and spread.*—An average of 47.6 cm in height and 44.2 cm in spread as a 2-year-old plant in a container and about 1 m in height and width as a 3-year-old plant in the landscape.

*Hardiness.*—At least in U.S.D.A. Zones 5 to 9.

*Diseases and pests.*—No susceptibility or resistance to pests and diseases has been observed.

*Root description.*—Fibrous and fine, 199D in color.

*Propagation.*—Stem cuttings.

*Time required for root development.*—An average of 6 weeks for root initiation with a young rooted plant produced in an average of 18 weeks.

*Growth rate.*—Moderate.

Stem description:

*Stem shape.*—Rounded.

*Stem strength.*—Strong.

*Stem aspect.*—Upright to an average angle of 75° to soil level (=0°).

*Stem color.*—Immature stems; 143C, mature stems; 146D and tinged at internodes with 200B, older bark; N199A and N200B to N200C.

*Stem size.*—An average of 29.5 cm (excluding the inflorescence) in length and 6 mm in diameter.

*Stem surface.*—Immature and mature stems; glabrous and densely lenticellate with lenticels; an average of 3 mm in length, 0.8 mm in width, 200A in color.

*Branching.*—Moderately branched with an average of 9 lateral branches, branching improves with pinching.

*Stem fasciation.*—None.

*Internode length.*—An average of 6.6 cm.

Foliage description:

*Leaf shape.*—Broad ovate.

*Leaf arrangement.*—Opposite.

*Leaf division.*—Simple.

*Leaf number.*—An average of 12 (6 pairs) per lateral branch.

*Leaf base.*—Truncate to cordate.

*Leaf apex.*—Apiculate.

*Leaf margins.*—Serrate.

*Leaf venation.*—Pinnate, color; mature upper surface 146D in color, mature lower surface slightly lighter than 146D with base of the mid rib vein having spots of anthocyanin in between N186C and 200A in color.

*Leaf size.*—An average of 8.5 cm in length and 6.8 cm in width.

*Leaf attachment.*—Petiolate.

*Leaf surface.*—Upper surface; smooth and slightly rugose, lower surface; smooth, slightly to moderately rugose.

*Leaf color.*—Young leaves upper surface; a color between 137A and 143B with some margins N186C in color, young lower surface; a color between 146B and 147B with some margins N186C in color, mature upper surface; NN137B with outer margin a color between N186C and 200A, mature lower surface; 148B with outer margin a color between N186C and 200A.

*Petioles.*—An average of 8 mm in length and 4 mm in diameter, color on upper surface slightly lighter than 146D, surface; smooth and matte and color on lower surface 144B and moderately covered with small lenticels; an average of 0.5 mm in length and 0.25 mm in width, and a color between N186C and 200A, surface; smooth and very slightly glossy.

Inflorescence description:

*Inflorescence type*.—Flattened globular, mophead type, compound corymb of rotate-shaped sterile flowers over inconspicuous fertile flowers.

*Lastingness of inflorescence*.—Sterile flowers; an average of 6 weeks, persistent, fertile flowers; an average of 2 days, self-cleaning.

*Lastingness as a cut flower*.—About 2 weeks in full color, longer as a drying inflorescence.

*Inflorescence number*.—One per lateral stem.

*Inflorescence size*.—An average of 10.7 cm in height and 16.4 cm in diameter.

*Flower number*.—An average of 100 sterile flowers and 100 fertile flowers per inflorescence.

*Flower fragrance*.—None.

*Flower aspect*.—Sterile flowers; upright to outwards, fertile flowers; upright.

*Flower size*.—Sterile flowers; an average of 2.5 cm in diameter and 9 mm in depth, fertile flowers; an average of 7 mm in diameter and 4 mm in depth.

*Flower shape*.—Sterile flowers; rotate, fertile flowers; rotate, petals drop when maturing.

*Flower buds*.—Sterile flowers; an average of 9 mm in length and 1.3 cm in diameter, narrow bowl-shaped, color; 145B tinged with 60C, fertile flowers; an average of 5 mm in length and 4 mm in diameter, obovate in shape, color; 145A and 60C at apex.

*Peduncles*.—An average of 8 cm in length and 5 mm in diameter, held upright to outwards, 64C in color, smooth surface, strong.

*Pedicels*.—Sterile flowers; an average of 1.6 cm in length and 1.5 mm in diameter, held at an average angle of 30° to peduncle (main peduncle=0°), 64C in color, moderately strong, surface is matt and moderately covered with thin pubescence; average of <0.2 mm in length and too small to measure color, fertile flowers; an average of 3 mm in length and 1 mm in diameter, held at an average angle of 10° to vertical, 70D in color, moderate strength, surface is matt and moderately covered with thin pubescence; average of <0.2 mm in length and too small to measure color.

*Petals*.—Sterile flowers; average of 4, rotate, ovate, strongly concave in shape, acute apex, cuneate base, entire margin, an average of 4 mm in length and 2.5 mm in width, glabrous and dull upper and lower surfaces, color when opening upper surface N80C and 76D toward apex, color when opening lower surface N80C, color when fully open upper surface N80C and 76D towards apex, color when fully open lower surface N80C, fertile flowers; average of 5, ovate in shape, concave, acute apex, cuneate base, entire margin, an average of 5 mm in length and 3 mm in width, glabrous and matt upper and lower surfaces, color when opening upper surface 146D, color when opening lower surface 145B fading lighter towards base to 145C to 145D, color when fully open upper surface 146D with margins 70C, color when fully open lower surface 145B with veins and margins 184A to 184B and 70C.

*Sepals*.—Sterile flowers; an average of 4, occasionally 5, rotate (cruciform) in arrangement, broad reniform to reniform in shape, moderate overlapping, apex is broadly blunt apiculate to un-deeply emarginate, cuneate base, margin irregular (observed on some sepals) coarsely crenate-serrate, and moderately to strong undulate, an average of 1.7 cm in length and 2.0 cm in width, color: upper surface when opening; 60D turning 60C towards apex, lower surface when opening; 70C tinged with 146D, upper surface when fully open; 61B and 61C towards apex, lower surface when fully open; 63C, upper surface when fading; 143A and 143B and mottled with 64D with veins 61C, lower surface when fading; 143C and 143D and 68C and 68D towards the base with veins 61C, both surfaces glabrous and matte, fertile flowers; an average of 5, rotate in arrangement, ovate in shape, acute apex, broadly cuneate base, entire margin, an average of 2 mm in length and 1.5 mm width, color when opening upper surface 144A to 144B, color when opening lower surface 145A to 145B, color when fully open upper and lower surface, 73D and 145A toward apex, upper surface glabrous and dull, lower surface glabrous and slightly glossy.

Reproductive organs:

*Gynoecium*.—Sterile flowers; 2 pistils, an average of 1.25 mm in length, stigma; club-shaped and NN155A in color, style; 1 mm in length, 75C in color, ovary is 155D in color, fertile flowers; an average of 3 pistils, an average of 2 mm in length, stigma; club-shaped and N155B in color, style; 1.5 mm in length and 76D in color, ovary is 150D in color.

*Androecium*.—Sterile flowers; an average of 8 stamens, filaments; an average of 4 mm in length and N155B in color, anthers; broad oblong in shape, an average of 1 mm in length and 155A in color, pollen; moderate in quantity, 158D in color, fertile flowers; an average of 10 stamens, filaments; an average of 3 mm in length and NN155D in color, anthers; oblong in shape, an average of 1 mm in length and 150D in color, pollen; moderate in quantity and 158D in color.

*Fruit and seed*.—None observed to date.

It is claimed:

1. A new and distinct cultivar of *Hydrangea* plant named 'Hokomareda' substantially as herein illustrated and described.

* * * * *